(12) United States Patent
Karlsson

(10) Patent No.: US 11,622,540 B2
(45) Date of Patent: Apr. 11, 2023

(54) AUTOMATED BEHAVIORAL AND PHYSIOLOGICAL TESTING OF UNTETHERED TESTING ANIMALS

(71) Applicant: SpikeGadgets, Inc., San Francisco, CA (US)

(72) Inventor: Hans Peter Mattias Karlsson, San Francisco, CA (US)

(73) Assignee: SpikeGadgets, Inc., San Francisco, CA (US)

( * ) Notice: Subject to any disclaimer, the term of this patent is extended or adjusted under 35 U.S.C. 154(b) by 155 days.

(21) Appl. No.: 17/000,071

(22) Filed: Aug. 21, 2020

(65) Prior Publication Data

US 2021/0051918 A1 Feb. 25, 2021

Related U.S. Application Data

(60) Provisional application No. 62/891,168, filed on Aug. 23, 2019.

(51) Int. Cl.
*A01K 29/00* (2006.01)
*G16H 10/40* (2018.01)

(52) U.S. Cl.
CPC .......... *A01K 29/005* (2013.01); *G16H 10/40* (2018.01)

(58) Field of Classification Search
CPC ...... A01K 29/005; A01K 1/0047; A01K 1/03; A01K 29/00; A01K 1/031; G16H 10/40
USPC .............................................. 119/482, 417
See application file for complete search history.

(56) References Cited

U.S. PATENT DOCUMENTS

| | | | | | |
|---|---|---|---|---|---|
| 4,593,650 | A | * | 6/1986 | Lattuada | A01K 1/031 119/419 |
| 5,247,901 | A | * | 9/1993 | Landon | A01K 1/031 119/419 |
| 5,474,030 | A | * | 12/1995 | Pittet | A23K 20/163 119/212 |
| 5,823,140 | A | * | 10/1998 | Pittet | B27N 3/00 224/908 |
| 5,868,928 | A | * | 2/1999 | Bradley | C12M 33/04 210/411 |

(Continued)

*Primary Examiner* — Yvonne R Abbott-Lewis
(74) *Attorney, Agent, or Firm* — Schwegman Lundberg & Woessner, P.A.

(57) ABSTRACT

Disclosed are systems, methods, and non-transitory computer-readable media for automated behavioral and physiological testing of untethered testing animals. An automated behavioral testing system communicates with electronic devices attached to testing animals to provide automated physiological measurements and perturbations. The electronic devices are wirelessly charged to eliminate the need to remove the electronic devices during the course of the study. The automated behavioral testing system includes a filtering chamber positioned between a housing chamber and a behavioral testing chamber. The filtering chamber provides a passageway between the housing chamber and the behavioral testing chamber used to manage access to the behavioral testing chamber. For example, a gate component implemented between the filtering chamber and the behavioral testing chamber can be configured into either a closed configuration to restrict access between the filtering chamber and the behavioral testing chamber, or an open configuration to permit between the filtering chamber and the behavioral testing chamber.

20 Claims, 11 Drawing Sheets

(56) References Cited

U.S. PATENT DOCUMENTS

| | | | |
|---|---|---|---|
| 2003/0116489 A1* | 6/2003 | Terato | A01K 63/045 |
| | | | 210/167.21 |
| 2004/0106101 A1* | 6/2004 | Evans | G01N 33/4836 |
| | | | 435/5 |
| 2009/0139459 A1* | 6/2009 | Habacivch | F41H 11/132 |
| | | | 119/420 |
| 2010/0331722 A1* | 12/2010 | Caudle | A01K 29/00 |
| | | | 600/557 |
| 2011/0070632 A1* | 3/2011 | Katoch | C12M 31/02 |
| | | | 15/4 |
| 2012/0048206 A1* | 3/2012 | Eakin | A01K 29/00 |
| | | | 119/51.01 |
| 2012/0180731 A1* | 7/2012 | Garner | A01K 1/031 |
| | | | 119/417 |
| 2012/0189549 A1* | 7/2012 | Claridge-Chang | A01K 29/005 |
| | | | 600/300 |
| 2014/0046222 A1* | 2/2014 | Yaksh | A61B 5/1123 |
| | | | 600/595 |
| 2014/0058214 A1* | 2/2014 | Woodward | A01K 1/03 |
| | | | 600/300 |
| 2015/0004898 A1* | 1/2015 | Desrochers | G01N 27/66 |
| | | | 454/239 |
| 2015/0112186 A1* | 4/2015 | Rapoport | G01R 33/583 |
| | | | 600/415 |
| 2018/0055434 A1* | 3/2018 | Cheung | A61B 5/16 |
| 2018/0084765 A1* | 3/2018 | Kanwal | A01K 61/85 |
| 2019/0141964 A1* | 5/2019 | Perslow | A01K 63/04 |
| | | | 119/211 |
| 2019/0147996 A1* | 5/2019 | Pulitzer | G16H 40/67 |
| | | | 705/2 |
| 2021/0076643 A1* | 3/2021 | Persaud | G06T 7/246 |
| 2021/0229946 A1* | 7/2021 | Knierim | B65H 59/385 |

* cited by examiner

AUTOMATED BEHAVIORAL AND PHYSIOLOGICAL TESTING OF UNTETHERED TESTING ANIMALS

CROSS-REFERENCE TO RELATED APPLICATIONS

This application claims the benefit of priority of U.S. Provisional Application No. 62/891,168, filed on Aug. 23, 2019, which is incorporated herein by reference in its entirety.

TECHNICAL FIELD

An embodiment of the present subject matter relates generally to behavioral testing and, more specifically, to automated behavioral testing.

BACKGROUND

Animals are commonly used in various scientific tests. For example, mice and rats are often used in neuroscience tests conducted to better understand the complex interactions between the brain, body, and environment. When conducting these types of scientific tests, the testing animals are generally housed in a cage and individually moved to a testing area as needed to conduct a test. As part of this process, each testing animal is often fitted with an electronic device that is used during the test. For example, the electronic device may capture data describing the testing animal during the test, provide electrical stimulation to the testing animal, provide drugs to the testing animal, and the like. After the test has been concluded, the electronic device is removed from the testing animal and the testing animal is returned to their cage. This process is repeated for each testing animal for the duration of the study. While effective, this process is both time consuming and resource intensive. Accordingly, improvements are needed.

BRIEF DESCRIPTION OF THE DRAWINGS

In the drawings, which are not necessarily drawn to scale, like numerals may describe similar components in different views. Like numerals having different letter suffixes may represent different instances of similar components. Some embodiments are illustrated by way of example, and not limitation, in the figures of the accompanying drawings in which.

DETAILED DESCRIPTION

Figure 1:
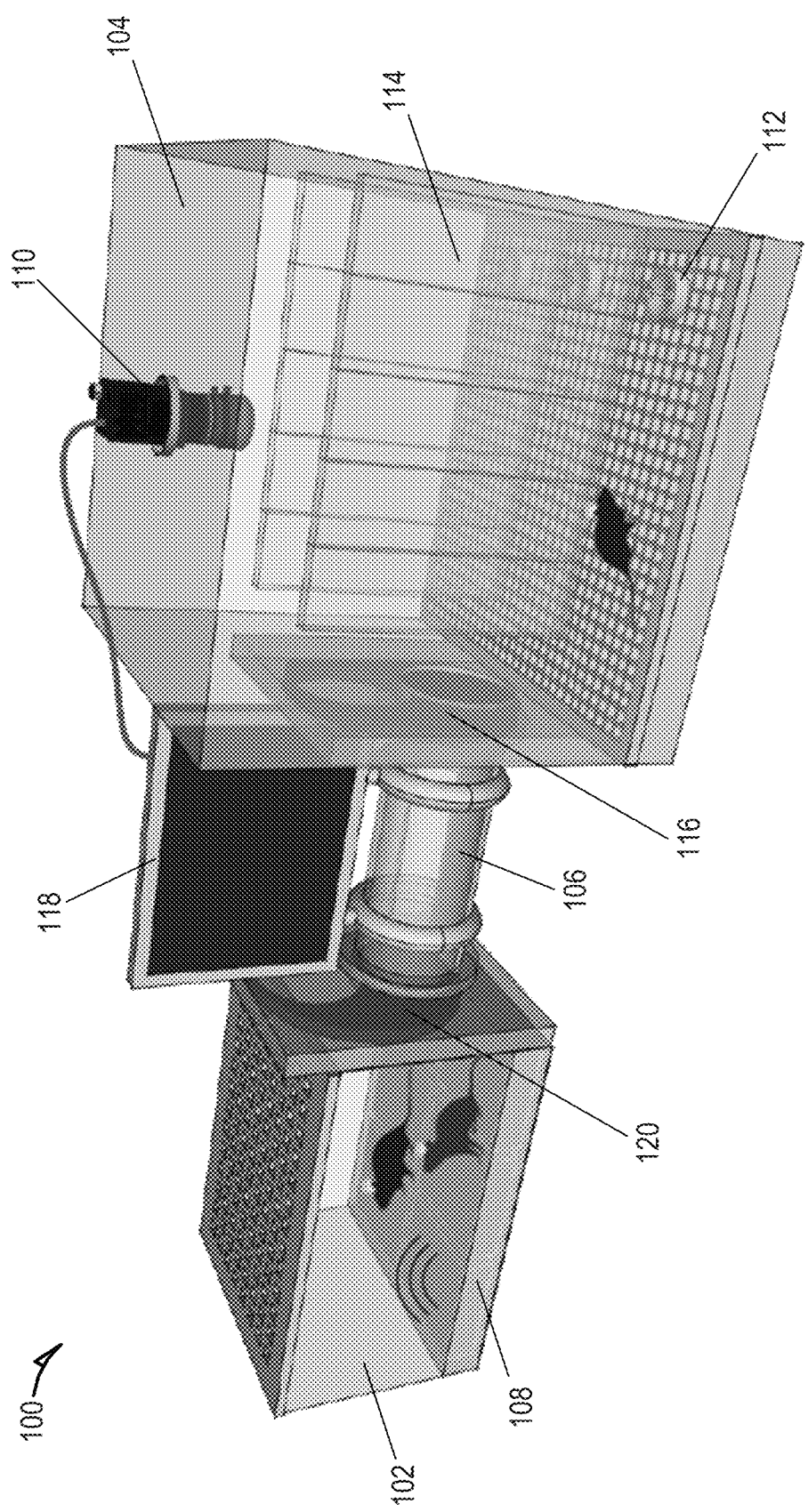
FIG. 1 shows an automated behavioral testing system, according to some example embodiments.

In the following description, for purposes of explanation, various details are set forth in order to provide a thorough understanding of some example embodiments. It will be apparent, however, to one skilled in the art, that the present subject matter may be practiced without these specific details, or with slight alterations.

Reference in the specification to "one embodiment" or "an embodiment" means that a particular feature, structure, or characteristic described in connection with the embodiment is included in at least one embodiment of the present subject matter. Thus, the appearances of the phrase "in one embodiment" or "in an embodiment" appearing in various places throughout the specification are not necessarily all referring to the same embodiment.

For purposes of explanation, specific configurations and details are set forth in order to provide a thorough understanding of the present subject matter. However, it will be apparent to one of ordinary skill in the art that embodiments of the subject matter described may be practiced without the specific details presented herein, or in various combinations, as described herein. Furthermore, well-known features may be omitted or simplified in order not to obscure the described embodiments. Various examples may be given throughout this description. These are merely descriptions of specific embodiments. The scope or meaning of the claims is not limited to the examples given.

Disclosed are systems, methods, and non-transitory computer-readable media for automated behavioral testing. An automated behavioral testing system includes a filtering chamber positioned between a housing chamber and a behavioral testing chamber. The housing chamber houses testing animals while the testing animals are not being tested. The behavioral testing chamber provides an environment in which the testing animals may be tested and observed. For example, the behavioral testing chamber may provide temporally-precise delivery of behavioral cues and liquid rewards, as well as behavioral event and task performance monitoring.

The filtering chamber provides a passageway between the housing chamber and the behavioral testing chamber and is used to manage access to the behavioral testing chamber by the testing animals. For example, a gate component positioned between the filtering chamber and the behavioral testing chamber can be configured into either a closed configuration to restrict access between the filtering chamber and the behavioral testing chamber, or an open configuration to permit movement between the filtering chamber and the behavioral testing chamber.

The automated behavioral testing system includes a test management system that modifies the configuration of the gate component to control the flow of the testing animals between the housing chamber and the behavioral testing chamber. For example, the automated behavioral testing system may include one or more sensors configured to capture sensor data in the filtering chamber. The test management system uses the sensor data to detect the presence of a testing animal in the filtering chamber. The test management system determines whether to allow the testing animal to enter the behavioral testing chamber based on a set of testing conditions. For example, the test management system may configure the gate component into an open configuration to allow the testing animal to enter the behavioral testing chamber when the testing conditions are determined to be satisfied. Alternatively, the gate component remains in a closed configuration when the testing conditions are not satisfied.

The testing conditions can be based on a variety of factors of combination of factors. For example, the testing conditions may be based on the number of testing animals detected in the filtering chamber, the weight of the testing animal, an amount of time that has elapsed since the testing animal was previously tested, whether another testing animal is present in the behavioral testing chamber, a battery level of an electronic device affixed to the testing animal, and the like. Use of the testing conditions allows for filtering of the testing animals into the behavioral testing chamber to be fully automated based on the defined conditions of a test administrator.

In addition to providing automated filtering of the testing animals into the behavioral testing chamber, the automated behavioral testing system also eliminates the need to repeatedly attach electronic devices to the testing animals prior to each test, remove the electronic devices after the test, and charge the individual electronic devices for use in subsequent tests. For example, the automated behavioral testing system includes a power charging source, such as an inductive coil, positioned in the housing chamber. The power charging source wirelessly charges the electronic devices affixed to each of the testing animals while the testing animals are present in the housing chamber. This allows for the electronic devices to remain attached to the testing animals throughout the duration of a study, rather than being removed after each test to be recharged.

FIG. 1 shows an automated behavioral testing system 100, according to some example embodiments. The automated behavioral testing system 100 allows for automated testing of testing animals during a scientific study. The testing animals may be any type of animal used to conduct scientific studies, such as rats, mice, monkey, dogs, cats, and the like. A scientific study may include multiple individual tests administered over a period of time. During each individual test, the behavior and/or physiology of one or more of the testing animals may be observed and/or recorded. For example, the behavior and/or physiology of a testing animal may be observed and/or recorded as the testing animal responds to a presented obstacle or challenge (e.g., maze). As another example, a testing animal may be administered with a drug or stimulant and the behavior and/or physiology of the response of testing animal may be observed and/or recorded.

As shown, the automated behavioral testing system 100 includes a housing chamber 102 and a behavioral testing chamber 104 connected by a filtering chamber 106. The housing chamber 102 provides housing for testing animals. For example, the housing chamber 102 may include standard housing items, such as bedding, water source (e.g., water bottle), air filter, enrichment objects (e.g., toys, running wheel), and the like. The housing chamber 102 may be used to house a single testing animal or multiple testing animals in a group environment.

The housing chamber 102 generally houses the testing animals while the testing animals are not being tested and/or observed as part of a study. Accordingly, during the course of a study, the testing animals generally spend the majority (e.g., 50%+) of their time in the housing chamber 102.

In some embodiments, the automated behavioral testing system 100 provides for untethered testing of the testing animals. That is, the testing animals are not physically tethered to a computer or power source via cords or cables. Rather, a battery powered or wirelessly powered electronic device is attached to each testing animal, which allows for unrestricted movement of the testing animals during the course of the study.

In current practice, battery powered electronic devices are manually removed from the testing animals to be recharged as needed, and then reattached to the testing animals to conduct further tests. This process is slow and laborious and can stress the research animals. To alleviate this issue, the automated behavioral testing system 100 provides for wireless charging of the electronic devices, thereby allowing for the electronic devices to remain attached to the testing animals during the entire duration of the study. For example, the automated behavioral testing system 100 includes a power charging source 108 positioned within an adequate proximity of the housing chamber 102 to wirelessly recharge the batteries of the electronic devices attached to the testing animals. The power charging source 108 may be any type of wireless charging device, such as an inductive coil.

The behavioral testing chamber 104 provides an environment in which testing animals may be tested and/or observed. For example, the behavioral testing chamber 104 may include sensors 110 for observing and/or capturing data describing the behavior of the testing animals, as well as testing response management components 112 for administering rewards to the testing animals. The sensors 110 may include any of a variety of types of sensors 110 used to observe and/or collected data describing a testing animal or an environment, such as video cameras, microphones, heat sensors, motion sensors, and the like.

The testing response management components 112 may be any type of apparatus or mechanism used to provide a desired testing response to a testing animal, such as a reward, adverse stimuli (e.g., electric shock) and the like. For example, a testing response management component 112 may simply be a bowl or stand that holds a reward, such as food, water or other liquid. Alternatively, a testing response management component 112 may be an electronic device that can detect the presence of a testing animal or a specific behavioral event and administer a reward, such as food, water or other liquid, or administer an adverse stimuli, such as an electric shock, bright lights, and/or loud sound.

A reward or adverse stimuli could also come in the form of direct neural perturbation of brain areas using by an electronic device mounted on the testing animal. For example, the electronic device can provide a perturbation to a specified area of the brain that is normally activated or inhibited by a reward. As another example, the electronic device can provide a perturbation to an area of the brain that elicits punishment. Such perturbations can be accomplished using electrical stimulation, drug delivery, optogenetics, chemogenetics, or other neural perturbation techniques.

In this type of embodiment, the testing response management components 112 may wirelessly communicate with the electronic device attached the testing animal to cause the perturbation. For example, the testing response management components 112 may communicate with the electronic device via a direct connection between the testing response management components 112 and the electronic device. Alternatively, the testing response management components 112 may communicate with the electronic device via the automated behavioral testing system 100. For example, the testing response management components 112 may communicate with components of the automated behavioral testing system 100 via a data receiver of the automated behavioral testing system 100. In turn, the automated behavioral testing system 100 may use a data transmitter to communicate with the electronic device attached to the testing animal to cause the specified perturbation.

The behavioral testing chamber 104 may also be configurable to create a desired test environment or configuration (e.g., test mode) for testing a testing animal. For example, the behavioral testing chamber 104 may allow for modular barriers 114 to be positioned within the behavioral testing chamber 104 as desired to create spatial mazes. Further, the position of the sensors 110 and the testing response management components 112 may be configured as desired within the behavioral testing chamber 104.

The filtering chamber 106 provides a passageway between the housing chamber 102 and the behavioral testing chamber 104 and is used to manage access to the behavioral testing chamber 104 by the testing animals. For example, a gate component 116 positioned between the filtering chamber 106 and the behavioral testing chamber 104 can be configured into either a closed configuration to restrict access between the filtering chamber 106 and the behavioral testing chamber 104, or an open configuration to permit access between the filtering chamber 106 and the behavioral testing chamber 104.

The gate component 116 may be any type of gate, door, or other barrier that is adequately sized to restrict a testing animal from passing between the filtering chamber 106 and the behavioral testing chamber 104 while the gate component is in the closed configuration. For example, the gate component 116 may be a rotary style door that includes a closed portion and an open portion. The gate component 116 may be attached to an actuator that modifies the position of the gate component 116 to cause the gate component to be modified from the closed configuration to the open configuration, and vice versa. For example, the actuator may be a motor that spins a rotary style door to cause either the open portion or the closed portion of the rotary style door to be positioned in an opening between the filtering chamber 106 and the behavioral testing chamber 104.

The automated behavioral testing system 100 includes a test management system 118 that automates the testing process, such as by automatically modifying the configuration of the gate component 116 to control the flow of the testing animals between the housing chamber 102 and the behavioral testing chamber 104. For example, to control access into the behavioral testing chamber 104 from the housing chamber 102, the gate component 116 may be primarily maintained in the closed configuration, and the test management system 118 modifies the configuration of the gate component 116 into the open configuration to allow one or more testing animals to enter the behavioral testing chamber 104 as desired for isolated testing and/or observation.

To accomplish this, the test management system 118 uses sensor data to detect the presence of a testing animal in the filtering chamber 106. For example, the automated behavioral testing system 100 may include sensors 110 positioned within and/or in proximity of the filtering chamber 106 that collect sensor data describing the filtering chamber 106. These sensors 110 may include a scale that detects the weight within the filtering chamber 106, a motion sensor that detects motion within the filtering chamber 106, a data receiver that detects data transmissions originating from within the filtering chamber 106, and the like. The test management system 118 uses this captured sensor data to determine whether a testing animal is present within the filtering chamber 106, such as by determining that the weight within the filtering chamber 106 exceeds a threshold weight, detecting motion within the filtering chamber 106, receiving a data transmission from within the filtering chamber 106, and the like.

Upon determining that a testing animal is present within the filtering chamber 106, the test management system 118 determines whether to allow the testing animal to enter the behavioral testing chamber 104 based on a set of testing conditions. The set of testing conditions define one or more individual conditions for allowing a testing animal to enter the behavioral testing chamber 104. The test management system 118 determines whether the set of testing conditions have been satisfied and, if so, modifies the configuration of the gate component 116 into the open configuration to allow the testing animal to enter the behavioral testing chamber 104. Alternatively, if the set of testing conditions are not satisfied, the test management system 118 does not modify the configuration of the gate component 116 such that the gate component 116 remains configured in the closed configuration to restrict the testing animal from accessing the behavioral testing chamber 104.

The set of testing conditions can include any of a variety of individual conditions or combination of conditions. For example, individual testing conditions may be based on the number of testing animals detected in the filtering chamber, the weight of the testing animal(s), an amount of time that has elapsed since the testing animal was previously tested, a battery level of an electronic device affixed to the testing animal, an amount of remaining memory available to the electronic device, and the like.

The test management system 118 may determine whether the set of testing conditions have been satisfied based on sensor data captured by sensors 110 of the automated behavioral testing system 100. For example, the test management system 118 may use sensor data captured by a scale that measures the weight in the filtering chamber 106 to determine the weight of the testing animal in the filtering chamber 106 and/or a number of testing animals in the filtering chamber 106.

As another example, the test management system 118 may use data transmissions captured by a data receiver that identify the testing animal and/or provide data regarding the electronic device attached to the testing animal. For example, the electronic component may include a transmitter that broadcasts a data transmission including a unique identifier associated with the testing animal, a current battery level of the electronic device, an available memory of a memory component (e.g, Secure Digital (SD) card) of the electronic device, and the like. As another example, a radio-frequency identification (WAD) tag may be affixed to the electronic device and/or testing animal and broadcast a unique identifier for the testing animal. As another example, the test management system 118 may use image data, video data and/or audio data captured using cameras and/or microphones to identify the testing animal and/or the number of testing animals in the filtering chamber 106.

In some embodiments, the automated behavioral testing system 100 may include a second gate component 120 positioned between the housing chamber 102 and the filtering chamber 106. Similar to the gate component 116 positioned between the filtering chamber 106 and the behavioral testing chamber 104, the gate component 120 positioned between the housing chamber 102 and the filtering chamber 106 may be configured into a closed configuration to restrict movement between the housing chamber 102 and the filtering chamber 106, or an open configuration to allow for movement between the housing chamber 102 and the filtering chamber 106.

The test management system 118 may modify the configuration of the second gate component to isolate and/or hold testing animals in the filtering chamber 106. For example, upon detecting that a testing animal has entered the filtering chamber 106 from the housing chamber 102, the test management system 118 may modify the configuration of the gate component 120 to a closed configuration to restrict the testing animal from returning to the housing chamber 102. This allows for isolation of the testing animal while sensor data is gathering (e.g., the testing animal is weighed) and/or while the test management system 118 determines whether to allow the testing animal to access the behavioral testing chamber 104.

The automated behavioral testing system 100 shown in FIG. 1 is just one example embodiment and is not meant to be limiting. For example, the automated behavioral testing system 100 may include multiple housing chambers 102, filtering chambers 106 and/or behavioral testing chambers 104. In embodiments in which the automated behavioral testing system 100 includes multiple housing chambers 102, testing animals may be housed in the various housing chambers 102 individually or in separate groups. As another example, the automated behavioral testing system 100 may include multiple behavioral testing chambers 104 for administering different tests. In these types of embodiments, the automated behavioral testing system 100 may include multiple gate components 116, 120 and filtering chambers 106 to properly filter testing animals into the appropriate housing chambers 102 and/or behavioral testing chambers 104. For example, each housing chamber 102 may be affixed to a filtering chamber 106 that provides a passageway directly into a behavioral testing chamber 104 or, alternatively, a filtering chamber 106 that provides a passageway to a secondary filtering chamber 106 that provides a passageway into one or more behavioral testing chambers 104.

Figure 2:
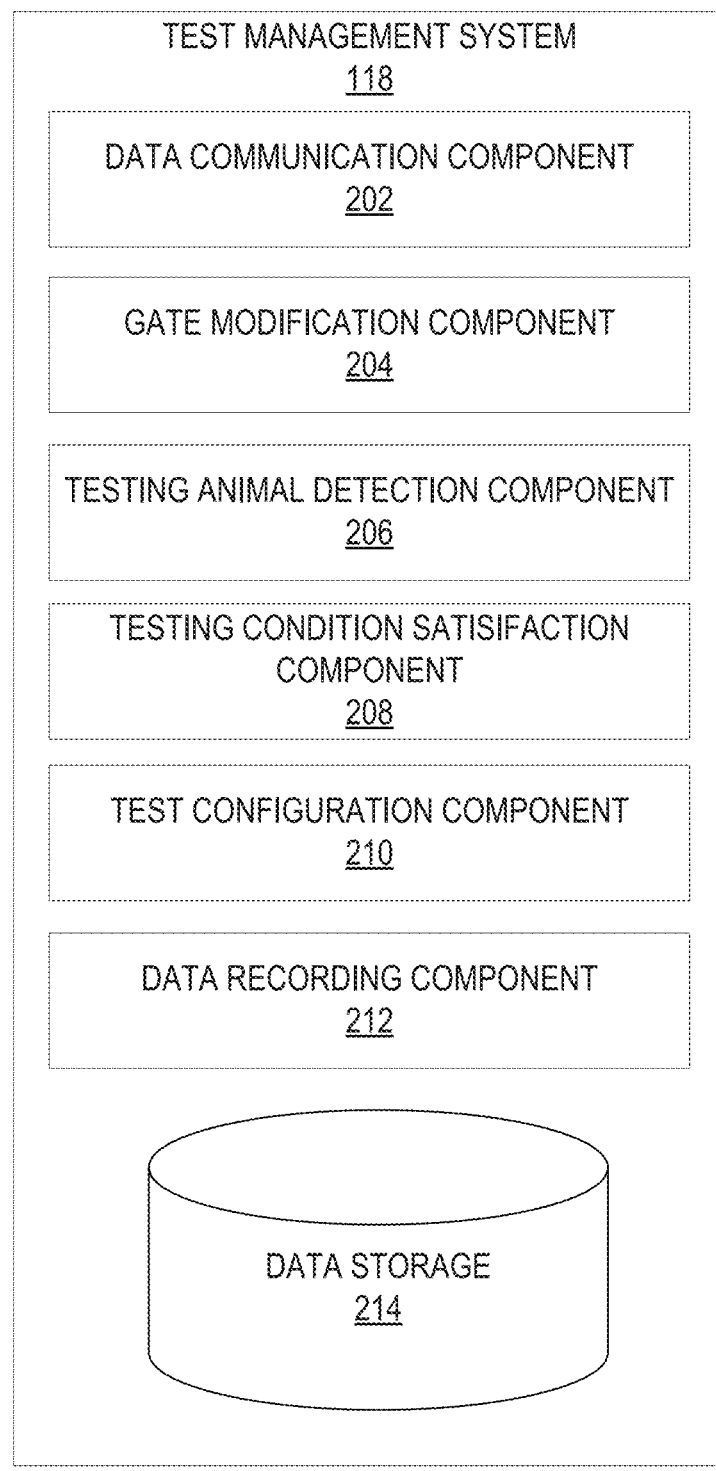
FIG. 2 is a block diagram of a behavioral testing system, according to some example embodiments.

FIG. 2. shows a block diagram of the test management system 118, according to some example embodiments. To avoid obscuring the inventive subject matter with unnecessary detail, various functional components (e.g., components) that are not germane to conveying an understanding of the inventive subject matter have been omitted from FIG. 2. However, a skilled artisan will readily recognize that various additional functional components may be supported by the test management system 118 to facilitate additional functionality that is not specifically described herein. Furthermore, the various functional components depicted in FIG. 2 may reside on a single computing device or may be distributed across several computing devices in various arrangements such as those used in cloud-based architectures.

The test management system 118 provides automated control of a scientific study using testing animals. For example, the test management system 118 modifies the configurations of gate components 116, 120 to properly filter testing animals into the behavioral testing chamber 104 to be tested, configures the behavioral testing chamber 104 for conducting tests, gathers sensor data describing the testing animals (e.g., weight, behavior, movement), and/or generates records describing the testing animals.

The test management system 118 may be connected to a communication network used to communicate with other devices/component (e.g., sensors 110, gate components 116, 120, testing response management components 112) connected to the communication network. The communication network can be comprised of any type of direct connection, such as a using cable, cords, and the like, or wireless network, including a local area network (LAN), such as an intranet, a wide area network (WAN), such as the internes, a telephone and mobile device network, such as cellular network, or any combination thereof. Further, the communication network may be a public network, a private network, or a combination thereof. The communication network can be implemented using any number of communication links associated with one or more service providers, including one or more wired communication links, one or more wireless communication links, or any combination thereof. Additionally, the communication network can be configured to support the transmission of data formatted using any number of protocols.

Multiple devices (e.g., computing devices, sensors 110, actuators, testing response management components 112) can be connected to the communication network. Each device may be any type of general computing device capable of network communication with other devices. For example, a device can be a personal computing device such as a desktop or workstation, a business server, or a portable computing device, such as a laptop, smart phone, or a tablet personal computer (PC). A device can include some or all of the features, components, and peripherals of the machine 1100 shown in FIG. 11.

To facilitate communication with other devices, a device can include a communication interface configured to receive a communication, such as a request, data, and the like, from another device in network communication with the device and pass the communication along to an appropriate module/component running on the device. The communication interface also sends a communication to another device in network communication with the device.

The test management system 118 may communicate with and concurrently accept communications from and initiate communication messages and/or interact with any number of devices, and support connections from a variety of different types of devices, such as actuators, computing devices, sensors, and the like. Hence, the devices may be of varying type, capabilities, operating systems, and so forth.

As shown, the test management system 118 includes a data communication component 202, a gate modification component 204, a testing animal detection component 206, a testing condition satisfaction component 208, a test configuration component 210, a data recording component 212, and a data storage 214.

The data communication component 202 facilitates communications with various devices, such as sensors 110 and/or electronic devices attached to testing animals. For example the data communication component 202 receives data used by the test management system 118, such as sensor data gathered by the various sensors 110 used by the automated behavioral testing system 100. This may include sensor data gathered by sensors 110 such as a scale, video camera, camera, microphone, motion sensor, and the like. The data communication component 202 may also receive data transmissions received from an electronic device attached to a testing animal. For example, the automated behavioral testing system 100 may include data receivers configured to receive data transmissions broadcasted by data transmitters used by the electronic devices attached to the testing animals. The data communication component 202 may provide the received data to the other components of the test management system 118.

The data communication component 202 may also communicate with the various sensors 110 and electronic devices. For example, the data communication component 202 may communicate with the various sensors 110 to cause initiation of the sensors 110, modify configuration of the sensors 110, and the like. Similarly, the data communication component 202 may communicate with the electronic devices attached to the testing animals. For example, the automated behavioral testing system 100 may include data transmitters configured to transmit data communications to the various electronic devices. These data transmissions may be used to request data from the electronic devices, such as a remaining power or memory level, as well as to cause the electronic devices to perform a specified action, such as administer a reward or adverse stimuli.

The gate modification component 204 modifies the configuration of a gate component 116, 120. An automated behavioral testing system 100 may include any number of gate components 116, 120 to control the flow of testing animal. For example, an automated behavioral testing system 100 may include a gate component 116 positioned between a filtering chamber 106 and a behavioral testing chamber 104 and/or a gate component 120 positioned between the filtering chamber 106 and the housing chamber 102. Further, the automated behavioral testing system 100 may include multiple housing chambers 102, filtering chambers 106 and/or behavioral testing chambers 104. Accordingly, the automated behavioral testing system 100 may include one or both of the described gate components 116, 120 positioned between any of the filtering chambers 106 and the housing chambers 102 and/or behavioral testing chambers 104.

Each gate component 116, 120 may be configured into either an open configuration or an closed configuration to control the movement of testing animals within the automated behavioral testing system 100. For example, a gate component 116, 120 may be configured into a closed configuration to restrict testing animals from passing from one chamber of the automated behavioral testing system 100 to another. Alternatively, a gate component 116, 120 may be configured into an open configuration to allow testing animals to pass from one chamber to another.

The gate modification component 204 causes a gate component 116, 120 to modify its configuration from one configuration to another, such as from the open configuration to a closed configuration or vice versa. For example, the gate modification component 204 transmits a command to an actuator associated with a gate component 116, 120 to cause the actuator to physically modify the position and/or orientation of the gate component 116, 120 to configure the gate component 116, 120 into either the open configuration or the closed configuration.

The gate modification component 204 may modify the configuration of a gate component 116, 120 in response to receiving a command to do so, such as a command from the other components of the test management system 118. Alternatively, the gate modification component 204 may modify the configuration of a gate component 116, 120 based a predetermined schedule. For example, the gate components may be configured into an open configuration during predetermined time periods when the testing animals are not being tested. Accordingly, the gate modification component 204 may cause the gate components 116, 120 to configure into the open configuration at the beginning of these predetermined time periods. Similarly, the gate modification component 204 may cause the gate components 116, 120 to configure into different configurations at the end of these predetermined time periods to resume testing of the test animals.

The testing animal detection component 206 determines when a testing animal has entered a filtering chamber 106. The testing animal detection component 206 accomplishes this using data gathered by the data communication component 202. For example, the testing animal detection component 206 determines that a testing animal is present in the filtering chamber 106 when the weight in the filtering chamber 106 has increased by a threshold amount and/or exceeds a threshold weight. As another example, the testing animal detection component 206 determines that a testing animal is present in the filtering chamber 106 when a data transmission is detected by a data receiver positioned within or near the filtering chamber 106. As another example, the testing animal detection component 206 determines that a testing animal is present in the filtering chamber 106 based on detected movements in the filtering chamber 106 as determined using motion sensors, optical sensors (e.g., video camera), and/or audio sensors (e.g., microphones) positioned within or near the filtering chamber 106.

The testing animal detection component 206 may communicate with the other components of the test management system 118 upon determining that a testing animal is present in the filtering chamber 106. For example, the testing animal detection component 206 may command the gate modification component 204 to modify a configuration of one or more of the gate components 116, 120. This can be performed to isolate the testing animal in the filtering chamber 106 and/or to restrict the movement of other testing animals.

The testing animal detection component 206 may also notify the testing condition satisfaction component 208 that a testing animal is present in the filtering chamber 106, such as when a testing animal has entered the filtering chamber 106 from the housing chamber 102. The testing condition satisfaction component 208 may then determine whether to allow the testing animal to enter the behavioral testing chamber 104 for testing. For example, the testing condition satisfaction component 208 permits testing animal to access the behavioral testing chamber 104 when a set of testing conditions are determined to have been satisfied.

As explained previously, the set of testing conditions define one or more individual testing conditions for allowing a testing animal to enter the behavioral testing chamber 104. The set of testing conditions can include any of a variety of individual testing conditions or combination of testing conditions. For example, individual testing conditions may be based on the number of testing animals detected in the filtering chamber, the weight of the testing animal(s), an amount of time that has elapsed since the testing animal was previously tested, a battery level of an electronic device affixed to the testing animal, an amount of remaining memory available to the electronic device, and the like.

The testing condition satisfaction component 208 accesses the set of testing conditions from the data storage 214. The testing condition satisfaction component 208 determines whether the set of testing conditions have been satisfied based on data gathered by the data communication component 202, such as sensor data and/or data transmissions broadcast by an electronic device attached to the testing animal. The testing condition satisfaction component 208 may also access data from the data storage 214, such as test logs for the testing animals.

Upon determining that the set of testing conditions have been satisfied, the testing condition satisfaction component 208 commands the gate modification component 204 to modify the configuration of the gate component 116 positioned between the filtering chamber 106 and the behavioral testing chamber 104 into an open configuration to allow the testing animal to enter the behavioral testing chamber 104. Alternatively, if the set of testing conditions have not been satisfied, the testing condition satisfaction component 208 does not provide the testing animal with access to the behavioral testing chamber 104. Rather, the testing animal detection component 206 may command the gate modification component 204 to modify the configuration of the gate component 120 positioned between the filtering chamber 106 and the housing chamber 102 into an open configuration to allow the testing animal to return to the housing chamber 102, as well as to allow other testing animals to enter the filtering chamber 106.

The test management system 118 may also automate the process of conducting a test. For example, the test configuration component 210 may cause the behavioral testing chamber 104 to be configured into a specified testing state. For example, the test configuration component 210 may communicate with testing response management components 112 and/or other components in the behavioral testing chamber 104 to cause the components to operate according to a specified test mode, initiate a specified performance, and the like.

The data recording component 212 generates testing data for a testing animal during a test. For example, the data recording component 212 uses data identifying the testing animal, such as a unique identifier, to identify a testing log associated with the testing animal. The data recording component 212 may update the testing log to indicate that the testing animal participated in a test. For example, the testing log may be updated with a timestamp that indicates the time of the test, a unique identifier identifying the testing animal that was tested, data identifying the type of test that was administered, and the like.

The data recording component 212 may also update the testing log with data describing the behavior of the testing animal during the test. For example, the data recording component 212 may receive sensor data from sensors 110 positioned to capture sensor data describing the testing animal's behavior during the test. For example, the data recording component 212 may receive video and/or image data from a camera located in the behavioral testing chamber 104. As another example, the data recording component 212 may also receive audio data from a microphone located in the behavioral testing chamber 104.

Figure 3:
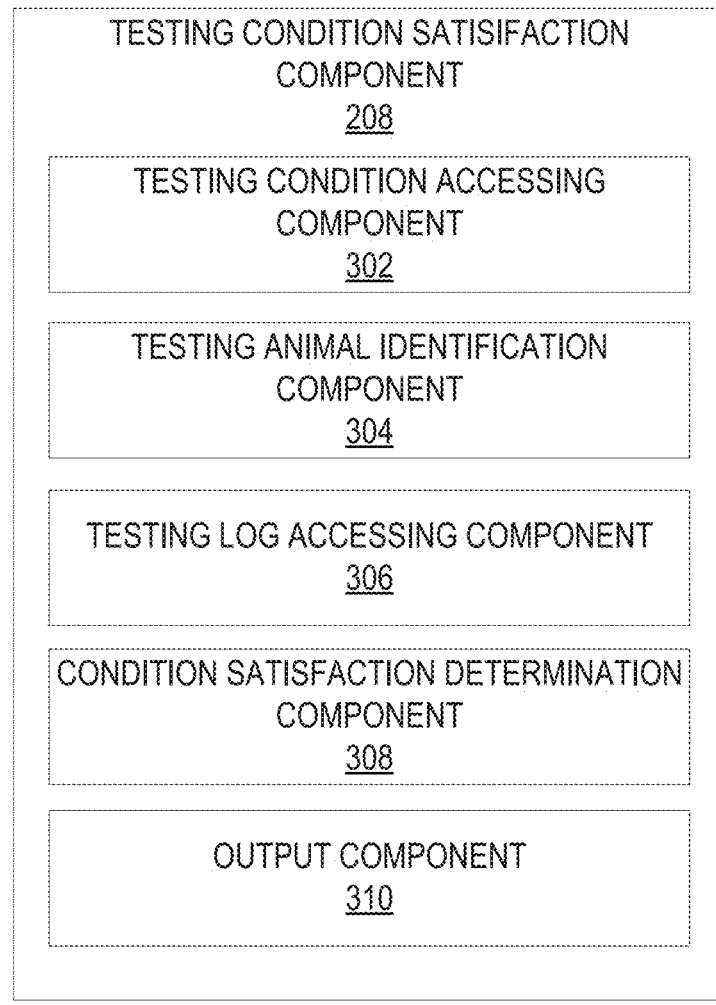
FIG. 3 is a block diagram of a testing condition satisfaction component, according to some example embodiments.

The data recording component 212 may also receive testing data from an electronic device attached to the testing animal. For example, the electronic device may include sensors capturing data describing the testing animal's physiology and/or behavior during the test. The electronic device may store the captured sensor data in a physical memory, such as an SD card, after which the stored data is provided to the test management system 118. Alternatively, the electronic device may transmit the sensor data to the data recording component 212 via a data transmitter, FIG. 3. shows a block diagram of the testing condition satisfaction component 208, according to some example embodiments. To avoid obscuring the inventive subject matter with unnecessary detail, various functional components (e.g., components) that are not germane to conveying an understanding of the inventive subject matter have been omitted from FIG. 3. However, a skilled artisan will readily recognize that various additional functional components may be supported by the testing condition satisfaction component 208 to facilitate additional functionality that is not specifically described herein. Furthermore, the various functional components depicted in FIG. 3 may reside on a single computing device or may be distributed across several computing devices in various arrangements such as those used in cloud-based architectures.

As shown, the testing condition satisfaction component 208 includes a testing condition accessing component 302, a testing animal identification component 304, a testing log accessing component 306, a condition satisfaction determination component 308 and an output component 310.

The testing condition accessing component 302 accesses the set of testing conditions from the data storage 214. The set of testing conditions define one or more individual conditions for allowing a testing animal to enter the behavioral testing chamber 104.

The testing animal identification component 304 identifies the testing animal or testing animals that are present in the filtering chamber 106. The testing animal identification component 304 may identify the testing animals in a number of ways. For example, in some embodiments, the testing animal identification component 304 may identify the testing animals based on a data transmission received from the testing animal. An RFID tag, or similar type of device, may be affixed to the testing animal and/or the electronic device attached to the testing animal. The RFID tag broadcast a unique identifier that identifies the testing animal. This data broadcast is captured by a data receiver provided to the testing animal identification component 304. The testing animal identification component 304 may then use the unique identifier to identify the testing animal that is present in the filtering chamber 106.

In some embodiments, the testing animal identification component 304 may identify the testing animal present in the filtering chamber 106 based on video captured by the optical sensors (e.g., cameras). For example, a readable code, such as a bar code, quick response (QR) code, and the like, may be attached to the testing animals. The readable code may store the unique identifier associated with the testing animal to which the readable code is attached. An optical sensor positioned to capture image data from the filtering chamber 106 may capture images of the readable code, which are then provided to the testing animal identification component 304. The testing animal identification component 304 determines the unique identifier identifying the testing animal from the image readable code.

These are just two examples of how the testing animals in the filtering chamber 106 may be identified and are not meant to be limiting. The testing animal identification component 304 may use any of a variety of other known techniques to identify the testing animals, such as facial recognition.

The testing log accessing component 306 accesses a testing log for a testing animal. The testing log for a testing animal includes testing data associated with the testing animal. For example, the testing data included in the testing log may include testing data describing the physiological response and/or behavior of the testing animal during tests. The testing log accessing component 306 accessed the testing log from the data storage 214 using a unique identifier associated with the testing animal. For example, the testing animal identification component 304 may provide the testing log accessing component 306 with the unique identifier identifying the testing animal present in the filtering chamber 106. The testing log accessing component 306 uses the unique identifier to retrieve a testing log corresponding to the unique identifier from the data storage 214.

The condition satisfaction determination component 308 determines whether a set of testing conditions have been satisfied. For example, the condition satisfaction determination component 308 determines whether the individual testing conditions included in the set of testing conditions have been satisfied based on data gathered from sensors 110, received in a data transmission (e.g., from an electronic device attached to the testing animal), and/or from testing data in the testing log.

In some embodiments, the condition satisfaction determination component 308 may determine whether a testing condition is satisfied based on comparisons with threshold values. For example, a testing condition may specify that a weight of a testing animal be equal to or greater than a threshold value. In this type of embodiment, the condition satisfaction determination component 308 accesses sensor data captured by a scale in the filtering chamber 106 that indicates the weight of the testing animal and compares the weight to a threshold weight value. If the weight meets or exceeds the threshold weight, the condition satisfaction determination component 308 determines that the testing condition has been satisfied. Alternatively, if the weight is below the threshold value, the condition satisfaction determination component 308 determines that the testing condition has not been satisfied.

The condition satisfaction determination component 308 may similarly use threshold values to determine whether other testing conditions have been satisfied. For example, a testing condition may dictate that an amount of memory available to the electronic device be equal to or greater than an threshold amount, that a number of testing animals in the filtering chamber 106 be no greater than a threshold amount, that a remaining power level of the electronic device be equal to or greater than a threshold amount, and the like. Various example, determining whether a testing condition has been satisfied are described below in relation to FIGS. 5-9.

The output component 310 provides an output based on whether the set of testing conditions have been satisfied. For example, the output component 310 may provide a command to the gate modification component 204 to modify a configuration of one or more gate components 116, 120. In the event that the set of testing conditions have been satisfied, the output component 310 may command the gate modification component 204 to modify the configuration of the gate component 116 positioned between the filtering chamber 106 and the behavioral testing chamber 104 into an open configuration to allow the testing animal to enter the behavioral testing chamber 104 to be tested. Alternatively, if the set of testing conditions have not been satisfied, the output component 310 may command the gate modification component 204 to modify the configuration of the gate component 120 positioned between the filtering chamber 106 and the housing chamber 102 into the open configuration to allow the testing animal to return to the housing chamber 102.

Figure 4:
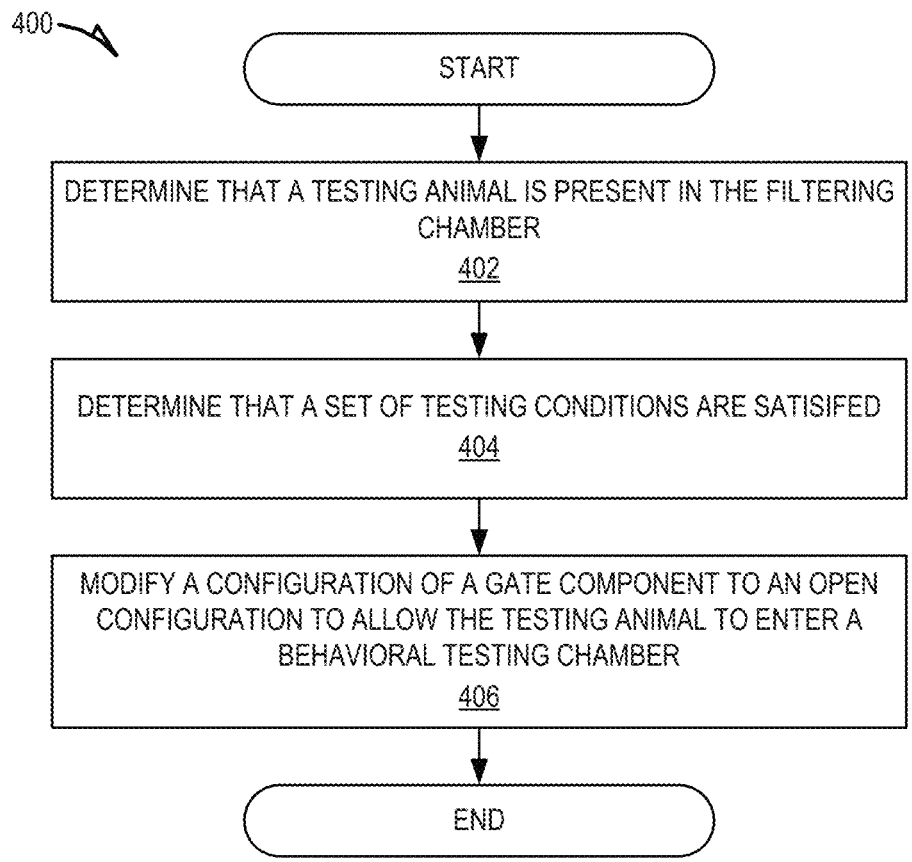
FIG. 4 is a flowchart showing a method for automated behavioral testing, according to some example embodiments.

FIG. 4 is a flowchart showing a method 400 for automated behavioral testing, according to some example embodiments. The method 400 may be embodied in computer readable instructions for execution by one or more processors such that the operations of the method may be performed in part or in whole by the testing condition satisfaction component 208; accordingly, the method is described below by way of example with reference thereto. However, it shall be appreciated that at least some of the operations of the methods may be deployed on various other hardware configurations and the methods are not intended to be limited to the testing condition satisfaction component 208.

At operation 402, the testing animal detection component 206 determines that a testing animal is present in the filtering chamber 106. The testing animal detection component 206 accomplishes this using data gathered by the data communication component 202. For example, the testing animal detection component 206 determines that a testing animal is present in the filtering chamber 106 when the weight in the filtering chamber 106 has increased by a threshold amount and/or exceeds a threshold weight. As another example, the testing animal detection component 206 determines that a testing animal is present in the filtering chamber 106 when a data transmission is detected by a data received positioned within or near the filtering chamber 106. As another example, the testing animal detection component 206 determines that a testing animal is present in the filtering chamber 106 based on detected movements in the filtering chamber 106 as determined using motion sensors, optical sensors (e.g., video camera), and/or audio sensors (e.g., microphones) positioned within or near the filtering chamber 106.

At operation 404, the testing condition satisfaction component 208 determines that a set of testing conditions are satisfied. The testing condition satisfaction component 208 permits testing animals to access the behavioral testing chamber 104 when a set of testing conditions are determined to have been satisfied.

As explained previously, the set of testing conditions define one or more individual conditions for allowing a testing animal to enter the behavioral testing chamber 104. The set of testing conditions can include any of a variety of individual conditions or combination of conditions. For example, individual testing conditions may be based on the number of testing animals detected in the filtering chamber, the weight of the testing animal(s), an amount of time that has elapsed since the testing animal was previously tested, a battery level of an electronic device affixed to the testing animal, an amount of remaining memory available to the electronic device, and the like.

The testing condition satisfaction component 208 accesses the set of testing conditions from the data storage 214. The testing condition satisfaction component 208 determines whether the set of testing conditions have been satisfied based on data gathered by the data communication component 202, such as sensor data and/or data transmissions broadcast by an electronic device attached to the testing animal. The testing condition satisfaction component 208 may also access data from the data storage 214, such as tests logs for the testing animals. Various example, determining whether a testing condition has been satisfied are described below in relation to FIGS. 5-9.

At operation 406, the gate modification component 204 modifies a configuration of a gate component 116 to an open configuration to allow the testing animal to enter a behavioral testing chamber 104. Upon determining that the set of testing conditions have been satisfied, the testing condition satisfaction component 208 commands the gate modification component 204 to modify the configuration of the gate component 116 positioned between the filtering chamber 106 and the behavioral testing chamber 104 into an open configuration to allow the testing animal to enter the behavioral testing chamber 104. In response to receiving the command, the gate modification component 204 transmits a command to an actuator associated with a gate component 116 to cause the actuator to physically modify the position and/or orientation of the gate component 116 to configure the gate component 116 into the open configuration. This allows the testing animal that is within the filtering chamber 106 to enter the behavioral testing chamber 104. After the testing animal is determined to have entered the behavioral testing chamber 104 or a timeout occurs, the gate modification component 204 may modify the configuration of the gate component 116 back to the closed configuration.

FIGS. 5-9 are flowcharts showing methods for determining that a set of testing conditions have been satisfied, according to some example embodiments. Each method may be embodied in computer readable instructions for execution by one or more processors such that the operations of the method may be performed in part or in whole by the testing condition satisfaction component 208; accordingly, the method is described below by way of example with reference thereto. However, it shall be appreciated that at least some of the operations of the methods may be deployed on various other hardware configurations and the methods are not intended to be limited to the testing condition satisfaction component 208.

Figure 5:
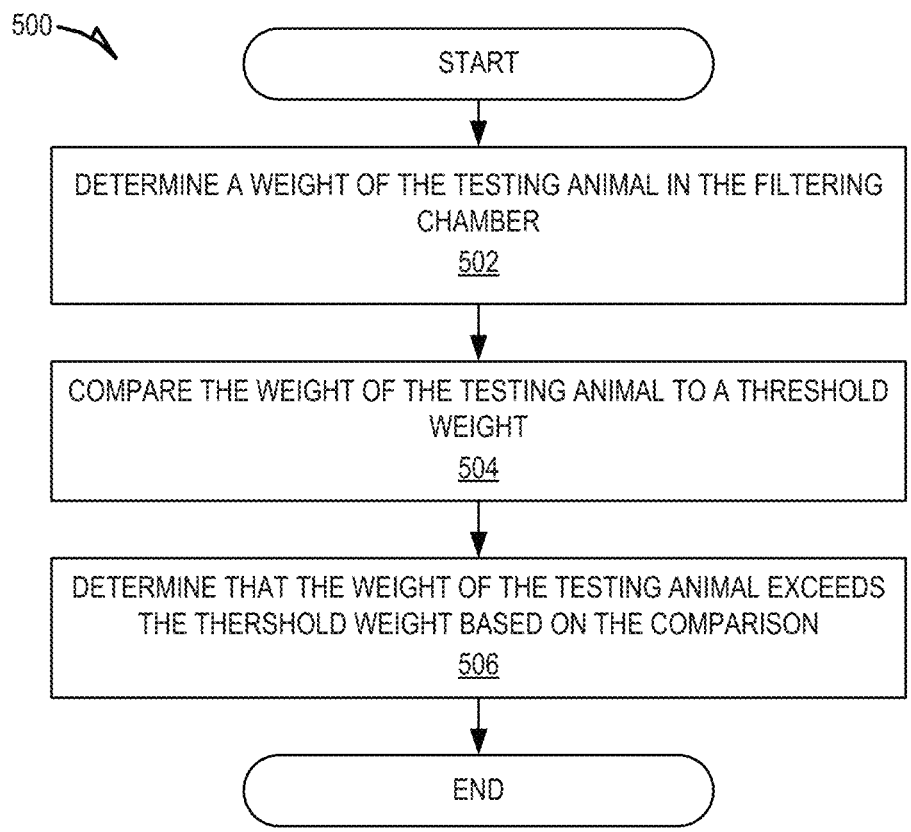
FIGS. 5-9 are flowcharts showing methods for determining that a set of testing conditions have been satisfied, according to some example embodiments.

FIG. 5 shows a method 500 for determining that a set of testing conditions are satisfied based on the weight of a testing animal.

At operation 502, the condition satisfaction determination component 308 determines a weight of a testing animal in the filtering chamber 106. The condition satisfaction determination component 308 determines the weight of the testing animal based on sensor data gathered by sensors 110 included in the automated behavioral testing system 100. For example, the sensors 110 may include a scale configured to measure the weight in the filtering chamber 106. The condition satisfaction determination component 308 accesses the sensor data captured by the scale to determine the weight of the testing animal that is present in the filtering chamber 106.

At operation 504, the condition satisfaction determination component 308 compares the weight of the testing animal to a threshold weight. The threshold weight may be defined in the set of testing conditions. For example, a testing condition may dictate that the weight of the testing animal meet or exceed a threshold weight. The testing condition accessing component 302 accesses the set of testing conditions from the data storage 214 and provides the set of testing conditions to the condition satisfaction determination component 308. In turn, the condition satisfaction determination component 308 determines the threshold weight from the set of testing conditions and compares the threshold weight to the weight of the testing animal that is in the filtering chamber 106.

At operation 506, the condition satisfaction determination component 308 determines that the weight of the testing animal exceeds the threshold weight based on the comparison. This may include determine that the weight of the testing animal is greater than the threshold weight or that the weight of the testing animal is equal to or greater than the threshold weight. The testing condition is satisfied when the weight of the testing animal exceeds the threshold weight. Alternatively, the testing condition is not satisfied when the weight of the testing animal is less than the threshold weight.

Figure 6:
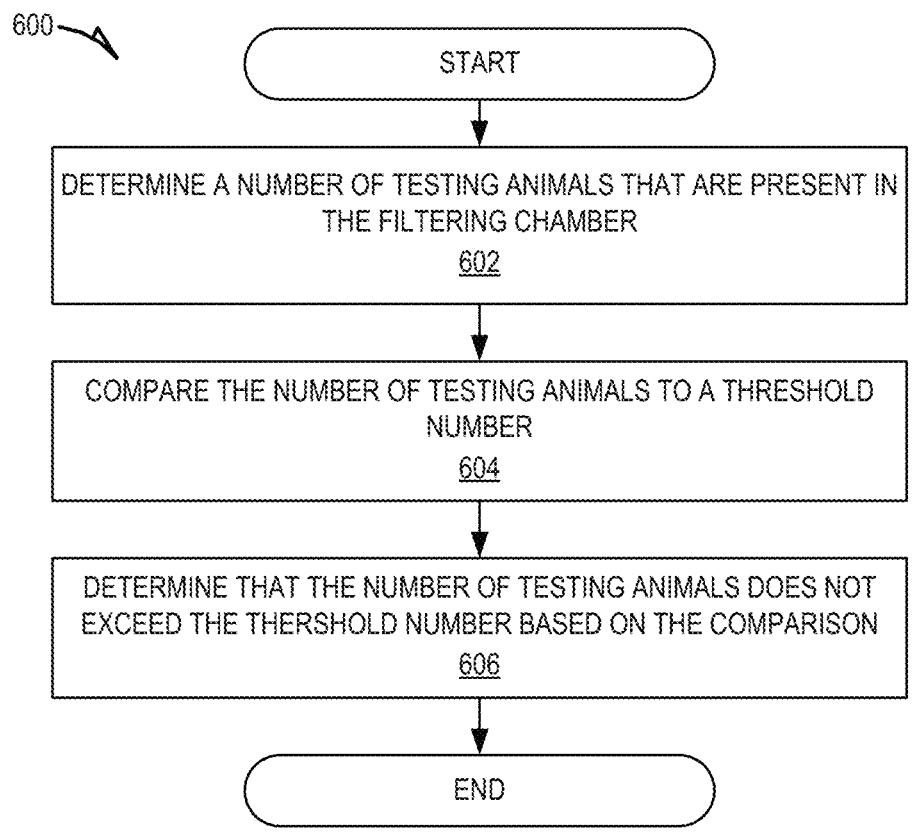

FIG. 6 shows a method 600 for determining that a set of testing conditions are satisfied based on a number of testing animals that are present in the filtering chamber.

At operation 602, the condition satisfaction determination component 308 determines a number of testing animals that are present in the filtering chamber 106. The condition satisfaction determination component 308 may determine the number of testing animals in the filtering chamber in several ways. For example, the condition satisfaction determination component 308 may determine the number of testing animals based on image data of the filtering chamber 106 captured by an optical sensor. The condition satisfaction determination component 308 may analyze the image data using object recognition techniques to identify individual testing animals present in the filtering chamber 106. Alternatively, the condition satisfaction determination component 308 may identify readable codes attached to the testing animals from the image data. In some embodiments, the condition satisfaction determination component 308 may determine the number of testing animals based on the number of unique identifiers received in data transmissions captured by a data receiver located in or nearby the filtering chamber 106.

At operation 604, the condition satisfaction determination component 308 compares the number of testing animals to a threshold number. The threshold number may be dictated by the set of testing conditions. For example, a testing condition may dictate a maximum number of testing animals that can be concurrently allowed to access the behavioral testing chamber 104 for testing. The condition satisfaction determination component 308 accesses the threshold number form the set of testing conditions and compares the threshold number to the number of testing animals determined to be in the filtering chamber 106.

At operation 606, the condition satisfaction determination component 308 determines that the number of testing animals does not exceed the threshold number based on the comparison. The testing condition is satisfied when the number of testing animals does not exceed the threshold number. Alternatively, the testing condition is not satisfied when the number of testing animals exceed the threshold number.

Figure 7:
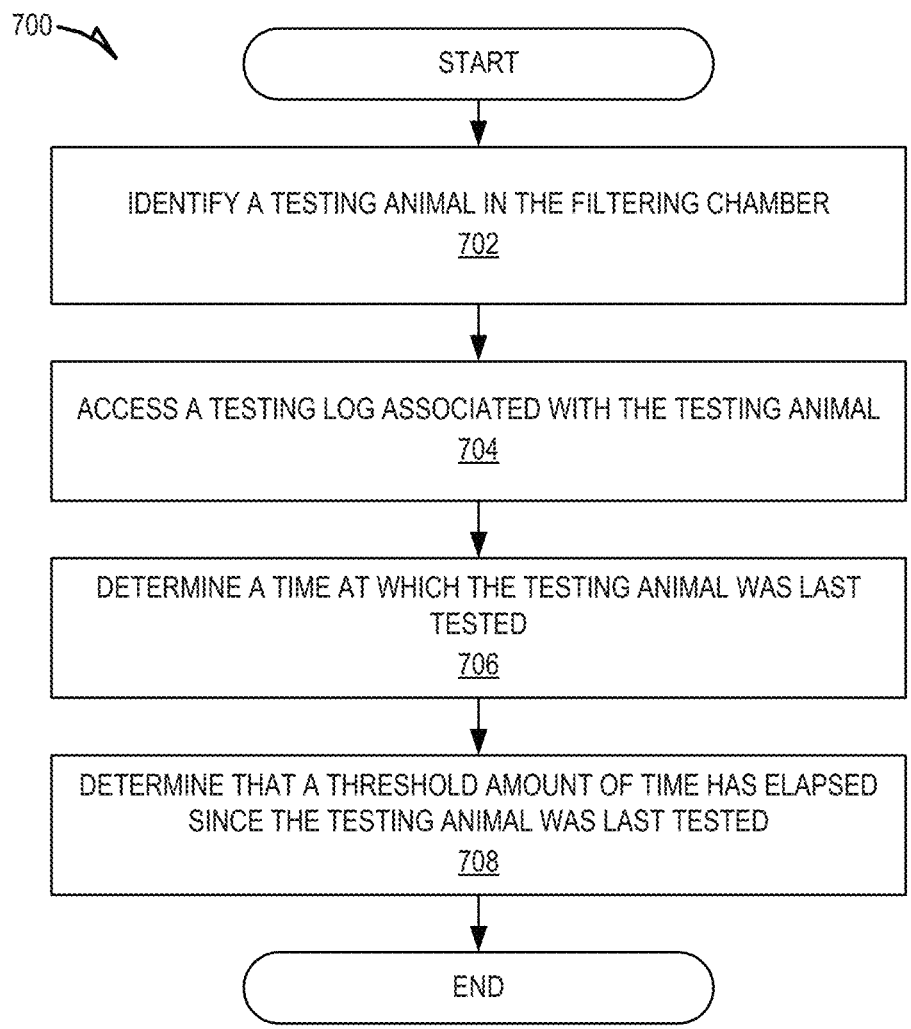

FIG. 7 shows a method 700 for determining that a set of testing conditions are satisfied based on a testing log associated with a testing animal.

At operation 702, the testing animal identification component 304. identifies a testing animal in the filtering chamber 106. The testing animal identification component 304 may identify the testing animal in a number of ways. For example, in some embodiments, the testing animal identification component 304 may identify the testing animal based on a data transmission received from the testing animal. An RFD tag, or similar type of device, may be affixed to the testing animal and/or the electronic device attached to the testing animal. The RFID tag broadcasts a unique identifier that identifies the testing animal. This data broadcast is captured by a data receiver and the captured data, including the unique identifier, is provided to the testing animal identification component 304. The testing animal identification component 304 may then use the unique identifier to identify the testing animal that is present in the filtering chamber 106.

In some embodiments, the testing animal identification component 304 may identify the testing animal present in the filtering chamber 106 based on video captured by the optical sensors (e.g., cameras). For example, a readable code, such as a bar code, quick response (QR) code, and the like, may be attached to the testing animals. The readable code may store the unique identifier associated with the testing animal to which the readable code is attached. An optical sensor positioned to capture image data from the filtering chamber 106 may capture images of the readable code, which are then provided to the testing animal identification component 304. The testing animal identification component 304 determines the unique identifier identifying the testing animal from the image readable code.

At operation 704, the testing log accessing component 306 accesses a testing log associated with the testing animal. The testing log for a testing animal includes testing data associated with the testing animal. For example, the testing data may include data describing the physiological response and/or behavior of the testing animal during tests. The testing log accessing component 306 accesses the testing log from the data storage 214 using the unique identifier associated with the testing animal. For example, the testing animal identification component 304 may provide the testing log accessing component 306 with the unique identifier identifying the testing animal present in the filtering chamber 106. The testing log accessing component 306 uses the unique identifier to retrieve the testing log corresponding to the unique identifier from the data storage 214.

At operation 706, the condition satisfaction determination component 308 determines a time at which the testing animal was last tested. The data log may include timestamp values indicating times at which testing data associated with the testing animal was logged. The condition satisfaction determination component 308 may use the timestamps to determines the time at which the testing animal was last tested.

At operation 708, the condition satisfaction determination component 308 determines that a threshold amount of time has elapsed since the testing animal was last tested. The threshold amount of time may be included in the set of testing conditions. For example, an individual testing condition may dictate that at least a threshold amount of time has to elapse between tests for a testing animal. The condition satisfaction determination component 308 determines the amount of elapsed time since the testing animal was last tested and compares the elapsed time to the threshold amount of time. The testing condition is determined to be satisfied when the elapsed time meets or exceeds the threshold amount of time.

Figure 8:
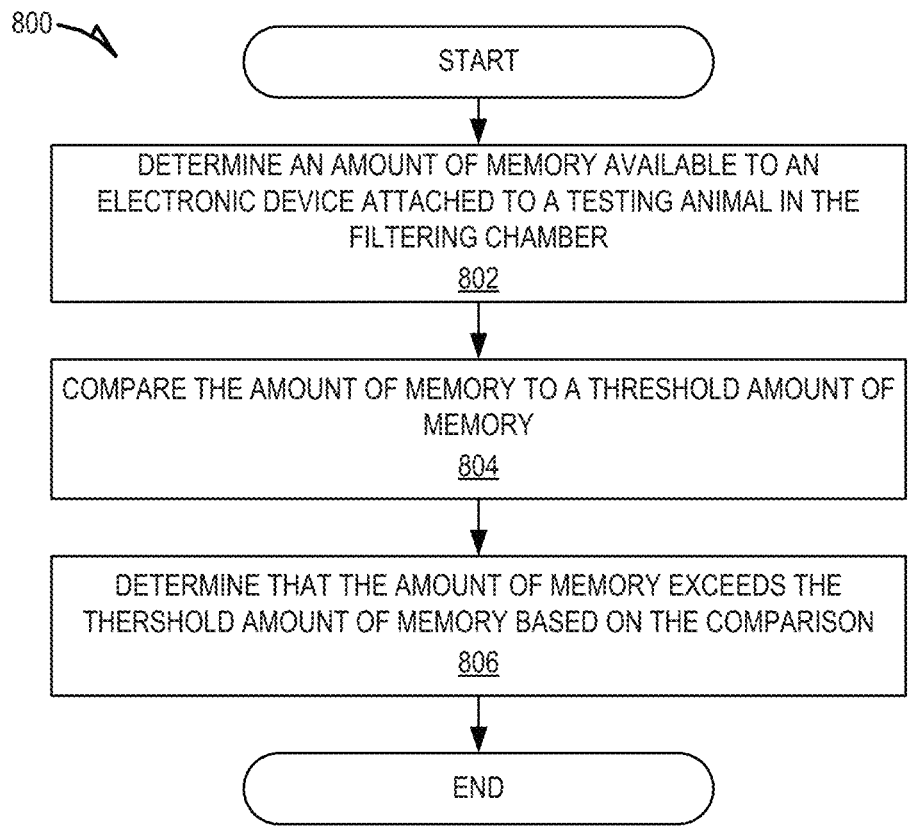

FIG. 8 shows a method 800 for determining that a set of testing conditions are satisfied based an amount of memory available to an electronic device attached to a testing animal.

At operation 802, the condition satisfaction determination component 308 determines an amount of memory available to an electronic device attached to a testing animal in the filtering chamber 106. The condition satisfaction determination component 308 may determine the amount of memory based on data transmission received from the electronic device. For example, the electronic device may include a data transceiver used to broadcast data, including the amount of remaining memory available to the electronic device. The amount of remaining memory may indicate an amount of memory remaining in a physical memory of the electronic device, such as an SD card.

At operation 804, the condition satisfaction determination component 308 compares the amount of memory to a threshold amount of memory. The threshold amount of memory may be identified in the set of testing conditions. For example, an individual testing condition may indicate that the the electronic device attached to a testing animal have at least a threshold amount of available memory. The condition satisfaction determination component 308 accesses the threshold amount from the set of testing conditions and compares it to the amount of memory remaining in a physical memory of the electronic device.

At operation 806, the condition satisfaction determination component 308 determines that the amount of remaining memory exceeds the threshold amount of memory based on the comparison. This may include determining that the amount or remaining memory is equal to or greater than the threshold amount. The testing condition is determined to be satisfied when the amount of remaining memory exceeds the threshold amount of memory.

Figure 9:
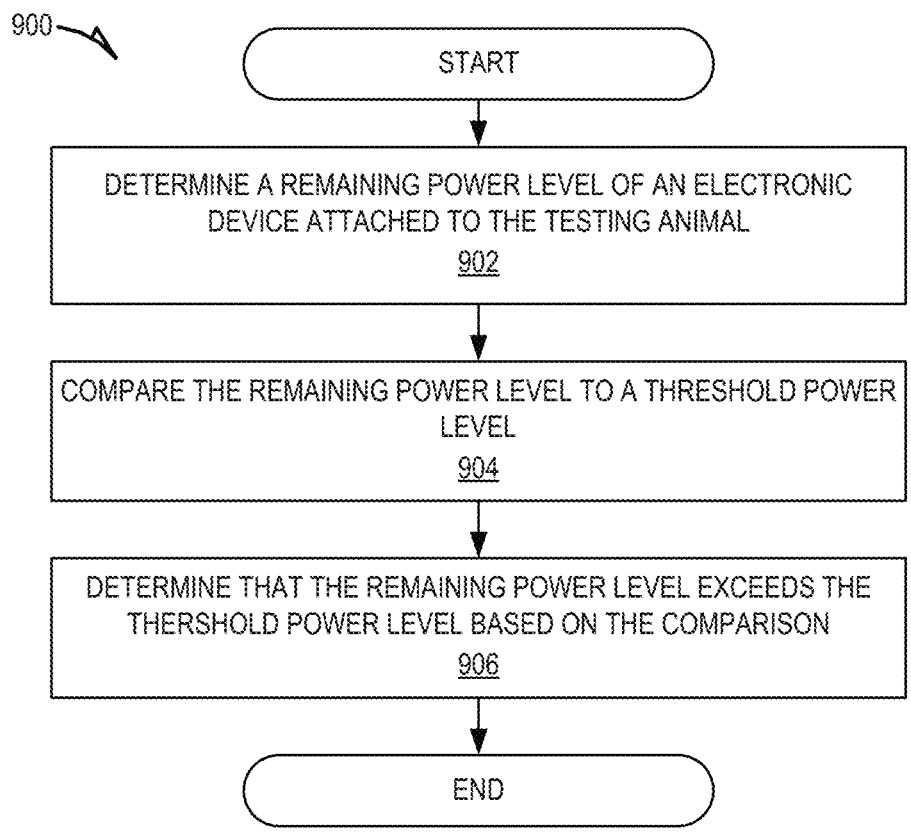

FIG. 9 shows a method 900 for determining that a set of testing conditions are satisfied based a remaining power level of an electronic device attached to a testing animal.

At operation 902, the condition satisfaction determination component 308 determines a remaining power level of an electronic device attached to a testing animal in the filtering chamber 106. The condition satisfaction determination component 308 may determine the remaining power level based on data transmission received from the electronic device. For example, the electronic device may include a data transceiver used to broadcast data, including the remaining power level available to the electronic device. The remaining power level may indicate an amount of power remaining in a physical battery used by the electronic device.

At operation 904, the condition satisfaction determination component 308 compares the remaining power level to a threshold power level. The threshold power level may be identified in the set of testing conditions. For example, an individual testing condition may indicate that the electronic device attached to a testing animal have at least a threshold power level. The condition satisfaction determination component 308 accesses the threshold power level from the set of testing conditions and compares it to the remaining power level of the physical battery of the electronic device.

At operation 906, the condition satisfaction determination component 308 determines that the remaining power level exceeds the threshold power level based on the comparison. This may include determining that the remaining power level is equal to or greater than the threshold power level. The testing condition is determined to be satisfied when the remaining power level exceeds (e.g., meets or exceeds) the threshold power level.

Software Architecture

Figure 10:
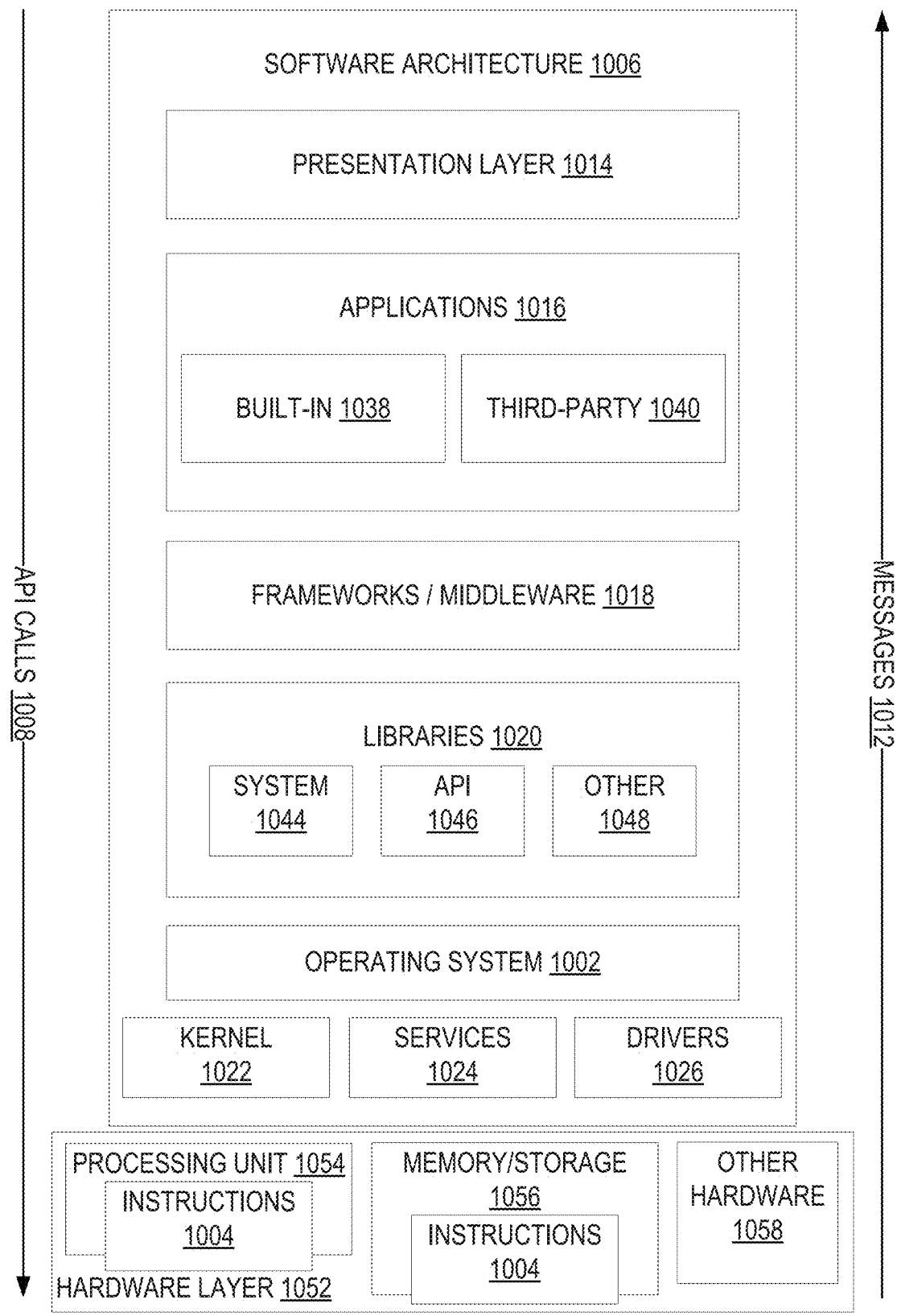
FIG. 10 is a block diagram illustrating components of a machine, according to some example embodiments, able to read instructions from a machine-readable medium (e.g., a machine-readable storage medium) and perform any one or more of the methodologies discussed herein.

FIG. 10 is a block diagram illustrating an example software architecture 1006, which may be used in conjunction with various hardware architectures herein described. FIG. 10 is a non-limiting example of a software architecture 1006 and it will be appreciated that many other architectures may be implemented to facilitate the functionality described herein. The software architecture 1006 may execute on hardware such as machine 1100 of FIG. 11 that includes, among other things, processors 1104, memory 1114, and (input/output) I/O components 1118. A representative hardware layer 1052 is illustrated and can represent, for example, the machine 1100 of FIG. 11. The representative hardware layer 1052 includes a processing unit 1054 having associated executable instructions 1004. Executable instructions 1004 represent the executable instructions of the software architecture 1006, including implementation of the methods, components, and so forth described herein. The hardware layer 1052 also includes memory and/or storage modules 1056, which also have executable instructions 1004. The hardware layer 1052 may also comprise other hardware 1058.

In the example architecture of FIG. 10, the software architecture 1006 may be conceptualized as a stack of layers where each layer provides particular functionality. For example, the software architecture 1006 may include layers such as an operating system 1002, libraries 1020, frameworks/middleware 1018, applications 1016, and a presentation layer 1014. Operationally, the applications 1016 and/or other components within the layers may invoke application programming interface (API) calls 1008 through the software stack and receive a response such as messages 1012 in response to the API calls 1008. The layers illustrated are representative in nature and not all software architectures have all layers. For example, some mobile or special purpose operating systems may not provide a frameworks/ middleware 1018, while others may provide such a layer. Other software architectures may include additional or different layers.

The operating system 1002 may manage hardware resources and provide common services. The operating system 1002 may include, for example, a kernel 1022, services 1024, and drivers 1026. The kernel 1022 may act as an abstraction layer between the hardware and the other software layers. For example, the kernel 1022 may be responsible for memory management, processor management (e.g., scheduling), component management, networking, security settings, and so on. The services 1024 may provide other common services for the other software layers. The drivers 1026 are responsible for controlling or interfacing with the underlying hardware. For instance, the drivers 1026 include display drivers, camera drivers, Bluetooth® drivers, flash memory drivers, serial communication drivers (e.g., Universal Serial Bus (USB) drivers), Wi-Fi® drivers, audio drivers, power management drivers, and so forth, depending on the hardware configuration.

The libraries 1020 provide a common infrastructure that is used by the applications 1016 and/or other components and/or layers. The libraries 1020 provide functionality that allows other software components to perform tasks in an easier fashion than to interface directly with the underlying operating system 1002 functionality (e.g., kernel 1022, services 1024, and/or drivers 1026). The libraries 1020 may include system libraries 1044 (e.g., C standard library) that may provide functions such as memory allocation functions, string manipulation functions, mathematical functions, and the like. In addition, the libraries 1020 may include API libraries 1046 such as media libraries (e.g., libraries to support presentation and manipulation of various media format such as MPEG4, H.264, MP3, AAC, AMR, PNG), graphics libraries (e.g., an OpenGL framework that may be used to render 2D and 3D in a graphic content on a display), database libraries (e.g., SQLite that may provide various relational database functions), web libraries (e.g., WebKit that may provide web browsing functionality), and the like. The libraries 1020 may also include a wide variety of other libraries 1048 to provide many other APIs to the applications 1016 and other software components/modules.

The frameworks/middleware 1018 (also sometimes referred to as middleware) provide a higher-level common infrastructure that may be used by the applications 1016 and/or other software components/modules. For example, the frameworks/middleware 1018 may provide various graphical user interface (GUI) functions, high-level resource management, high-level location services, and so forth. The frameworks/middleware 1018 may provide a broad spectrum of other APIs that may be used by the applications 1016 and/or other software components/modules, some of which may be specific to a particular operating system 1002 or platform.

The applications 1016 include built-in applications 1038 and/or third-party applications 1040. Examples of representative built-in applications 1038 may include, but are not limited to, a contacts application, a browser application, a book reader application, a location application, a media application, a messaging application, and/or a game application. Third-party applications 1040 may include an application developed using the ANDROID™ or IOS™ software development kit (SDK) by an entity other than the vendor of the particular platform, and may be mobile software running on a mobile operating system such as IOS™, ANDROID™, WINDOWS® Phone, or other mobile operating systems. The third-party applications 1040 may invoke the API calls 1008 provided by the mobile operating system (such as operating system 1002) to facilitate functionality described herein.

The applications 1016 may use built in operating system functions kernel 1022, services 1024, and/or drivers 1026), libraries 1020, and frameworks/middleware 1018 to create UIs to interact with users of the system. Alternatively, or additionally, in some systems, interactions with a user may occur through a presentation layer, such as presentation layer 1014. In these systems, the application/component "logic" can be separated from the aspects of the application/component that interact with a user.

Figure 11:
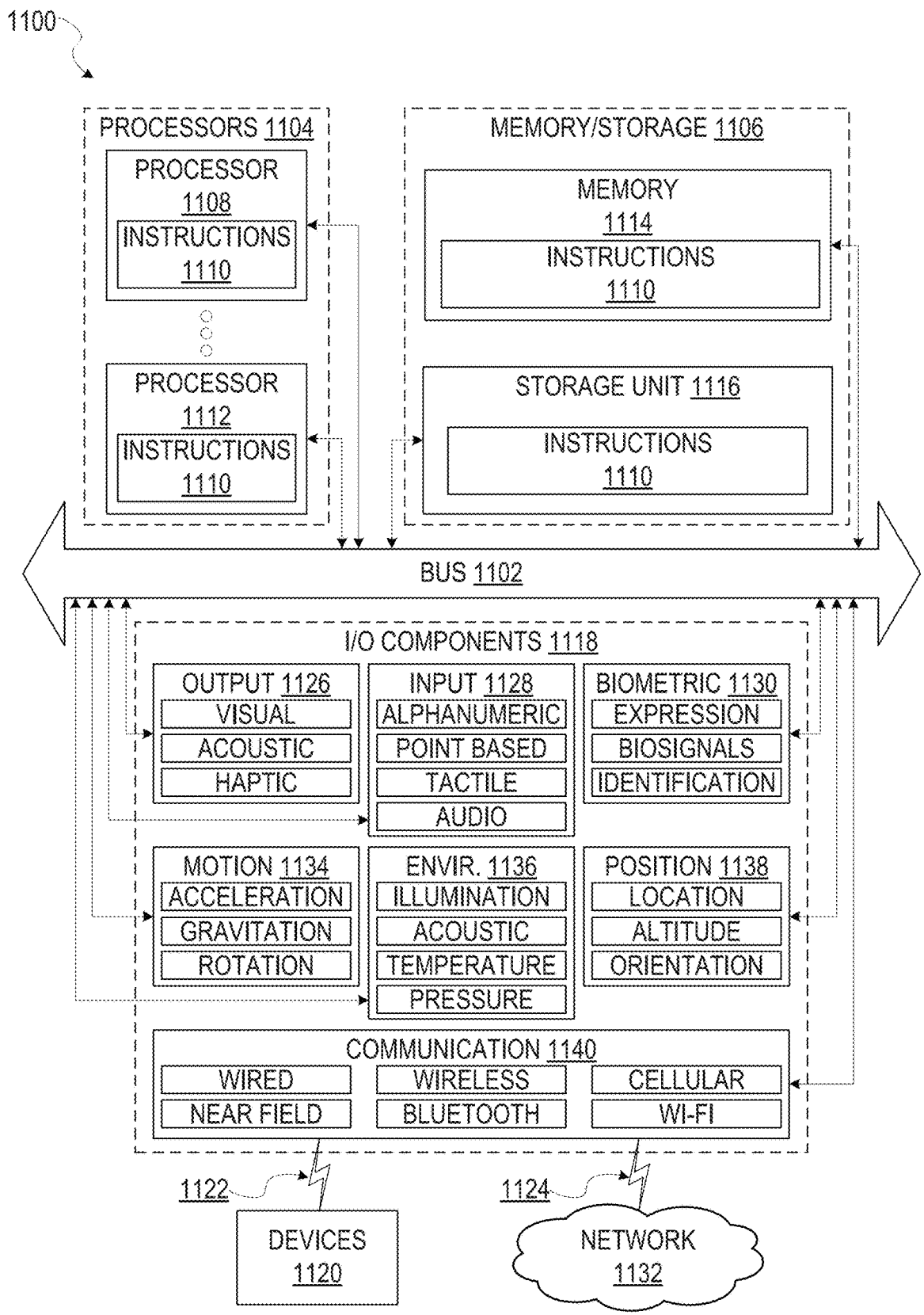
FIG. 11 is a block diagram illustrating components of a machine, according to some example embodiments, able to read instructions from a machine-readable medium (e.g., a machine-readable storage medium) and perform any one or more of the methodologies discussed herein.

FIG. 11 is a block diagram illustrating components of a machine 1100, according to some example embodiments, able to read instructions 1004 from a machine-readable medium (e.g., a machine-readable storage medium) and perform any one or more of the methodologies discussed herein. Specifically, FIG. 11 shows a diagrammatic representation of the machine 1100 in the example form of a computer system, within which instructions 1110 (e.g., software, a program, an application, an applet, an app, or other executable code) for causing the machine 1100 to perform any one or more of the methodologies discussed herein may be executed. As such, the instructions 1110 may be used to implement modules or components described herein. The instructions 1110 transform the general, non-programmed machine 1100 into a particular machine 1100 programmed to carry out the described and illustrated functions in the manner described. In alternative embodiments, the machine 1100 operates as a standalone device or may be coupled (e.g., networked) to other machines. In a networked deployment, the machine 1100 may operate in the capacity of a server machine or a client machine in a server-client network environment, or as a peer machine in a peer-to-peer (or distributed) network environment. The machine 1100 may comprise, but not be limited to, a server computer, a client computer, a PC, a tablet computer, a laptop computer, a netbook, a set-top box (STB), a personal digital assistant (PDA), an entertainment media system, a cellular telephone, a smart phone, a mobile device, a wearable device (e.g., a smart watch), a smart home device (e.g., a smart appliance), other smart devices, a web appliance, a network router, a network switch, a network bridge, or any machine 1100 capable of executing the instructions 1110, sequentially or otherwise, that specify actions to be taken by machine 1100. Further, while only a single machine 1100 is illustrated, the term "machine" shall also be taken to include a collection of machines that individually or jointly execute the instructions 1110 to perform any one or more of the methodologies discussed herein.

The machine 1100 may include processors 1104, memory/storage 1106, and 110 components 1118, which may be configured to communicate with each other such as via a bus 1102. The memory/storage 1106 may include a memory 1114, such as a main memory, or other memory storage, and a storage unit 1116, both accessible to the processors 1104 such as via the bus 1102. The storage unit 1116 and memory 1114 store the instructions 1110 embodying any one or more of the methodologies or functions described herein. The instructions 1110 may also reside, completely or partially, within the memory 1114, within the storage unit 1116, within at least one of the processors 1104 (e.g., within the processor's cache memory), or any suitable combination thereof, during execution thereof by the machine 1100. Accordingly, the memory 1114, the storage unit 1116, and the memory of processors 1104 are examples of machine-readable media.

The I/O components 1118 may include a wide variety of components to receive input, provide output, produce output, transmit information, exchange information, capture measurements, and so on. The specific I/O components 1118 that are included in a particular machine 1100 will depend on the type of machine. For example, portable machines such as mobile phones will likely include a touch input device or other such input mechanisms, while a headless server machine will likely not include such a touch input device. It will be appreciated that the I/O components 1118 may include many other components that are not shown in FIG. 11. The I/O components 1118 are grouped according to functionality merely for simplifying the following discussion and the grouping is in no way limiting. In various example embodiments, the I/O components 1118 may include output components 1126 and input components 1128. The output components 1126 may include visual components (e.g., a display such as a plasma display panel (PDP), a light emitting diode (LED) display, a liquid crystal display (LCD), a projector, or a cathode ray tube CRT)), acoustic components (e.g., speakers), haptic components (e.g., a vibratory motor, resistance mechanisms), other signal generators, and so forth. The input components 1128 may include alphanumeric input components (e.g., a keyboard, a touch screen configured to receive alphanumeric input, a photo-optical keyboard, or other alphanumeric input components), point based input components (e.g., a mouse, a touchpad, a trackball, a joystick, a motion sensor, or other pointing instrument), tactile input components (e.g., a physical button, a touch screen that provides location and/or force of touches or touch gestures, or other tactile input components), audio input components (e.g., a microphone), and the like.

In further example embodiments, the I/O components 1118 may include biometric components 1130, motion components 1134, environmental components 1136, or position components 1138 among a wide array of other components. For example, the biometric components 1130 may include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram based identification), and the like. The motion components 1134 may include acceleration sensor components (e.g., accelerometer), gravitation sensor components, rotation sensor components (e.g., gyroscope), and so forth. The environmental components 1136 may include, for example, illumination sensor components (e.g., photometer), temperature sensor components (e.g., one or more thermometer that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detect concentrations of hazardous gases for safety or to measure pollutants in the atmosphere), or other components that may provide indications, measurements, or signals corresponding to a surrounding physical environment. The position components 1138 may include location sensor components (e.g., a GPS receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 1118 may include communication components 1140 operable to couple the machine 1100 to a network 1132 or devices 1120 via coupling 1124 and coupling 1122, respectively. For example, the communication components 1140 may include a network interface component or other suitable device to interface with the network 1132. In further examples, communication components 1140 may include wired communication components, wireless communication components, cellular communication components, near field communication (NFC) components, Bluetooth® components (e.g., Bluetooth® Low Energy), Wi-Fi® components, and other communication components to provide communication via other modalities. The devices 1120 may be another machine or any of a wide variety of peripheral devices (e.g., a peripheral device coupled via a USB).

Moreover, the communication components 1140 may detect identifiers or include components operable to detect identifiers. For example, the communication components 1140 may include radio frequency identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 1140 such as location via Internet Protocol (IP) geo-location, location via Wi-Fi® signal triangulation, location via detecting a NEC beacon signal that may indicate a particular location, and so forth.

Glossary

"CARRIER SIGNAL" in this context refers to any intangible medium that is capable of storing, encoding, or carrying instructions 1110 for execution by the machine 1100, and includes digital or analog communications signals or other intangible medium to facilitate communication of such instructions 1110. Instructions 1110 may be transmitted or received over the network 1132 using a transmission medium via a network interface device and using any one of a number of well-known transfer protocols.

"CLIENT DEVICE" in this context refers to any machine 1100 that interfaces to a communications network 1132 to obtain resources from one or more server systems or other client devices. A client device may be, but is not limited to, mobile phones, desktop computers, laptops, PDAs, smart phones, tablets, ultra books, netbooks, laptops, multi-processor systems, microprocessor-based or programmable consumer electronics, game consoles, STBs, or any other communication device that a user may use to access a network 1132.

"COMMUNICATIONS NETWORK" in this context refers to one or more portions of a network 1132 that may be an ad hoc network, an intranet, an extranet, a virtual private network (VPN), a LAN, a wireless LAN (WLAN), a WAN, a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, a network 1132 or a portion of a network 1132 may include a wireless or cellular network and the coupling may be a Code Division Multiple Access (CDMA) connection, a Global System for Mobile communications (GSM) connection, or other type of cellular or wireless coupling. In this example, the coupling may implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard setting organizations, other long range protocols, or other data transfer technology.

"MACHINE-READABLE MEDIUM" in this context refers to a component, device or other tangible media able to store instructions 1110 and data temporarily or permanently and may include, but is not be limited to, random-access memory (RAM), read-only memory (ROM), buffer memory, flash memory, optical media, magnetic media, cache memory, other types of storage (e.g., erasable programmable read-only memory (EEPROM)), and/or any suitable combination thereof. The term "machine-readable medium" should be taken to include a single medium or multiple media (e.g., a centralized or distributed database, or associated caches and servers) able to store instructions 1110. The term "machine-readable medium" shall also be taken to include any medium, or combination of multiple media, that is capable of storing instructions 1110 (e.g., code) for execution by a machine 1100, such that the instructions 1110, when executed by one or more processors 1104 of the machine 1100, cause the machine 1100 to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" excludes signals per se.

"COMPONENT" in this context refers to a device, physical entity, or logic having boundaries defined by function or subroutine calls, branch points, APIs, or other technologies that provide for the partitioning or modularization of particular processing or control functions. Components may be combined via their interfaces with other components to carry out a machine process. A component may be a packaged functional hardware unit designed for use with other components and a part of a program that usually performs a particular function of related functions. Components may constitute either software components (e.g., code embodied on a machine-readable medium) or hardware components. A "hardware component" is a tangible unit capable of performing certain operations and may be configured or arranged in a certain physical manner. In various example embodiments, one or more computer systems (e.g., a standalone computer system, a client computer system, or a server computer system) or one or more hardware components of a computer system (e.g., a processor or a group of processors 1104) may be configured by software (e.g., an application 1016 or application portion) as a hardware component that operates to perform certain operations as described herein. A hardware component may also be implemented mechanically, electronically, or any suitable combination thereof. For example, a hardware component may include dedicated circuitry or logic that is permanently configured to perform certain operations. A hardware component may be a special-purpose processor, such as a field-programmable gate array (FPGA) or an application specific integrated circuit (ASIC). A hardware component may also include programmable logic or circuitry that is temporarily configured by software to perform certain operations. For example, a hardware component may include software executed by a general-purpose processor 1104 or other programmable processor 1104. Once configured by such software, hardware components become specific machines 1100 (or specific components of a machine 1100) uniquely tailored to perform the configured functions and are no longer general-purpose processors 1104. It will be appreciated that the decision to implement a hardware component mechanically, in dedicated and permanently configured circuitry, or in temporarily configured circuitry (e.g., configured by software), may be driven by cost and time considerations. Accordingly, the phrase "hardware component" (or "hardware-implemented component") should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware components are temporarily configured (e.g., programmed), each of the hardware components need not be configured or instantiated at any one instance in time. For example, where a hardware component comprises a general-purpose processor 1104 configured by software to become a special-purpose processor, the general-purpose processor 1104 may be configured as respectively different special-purpose processors (e.g., comprising different hardware components) at different times. Software accordingly configures a particular processor or processors 1104, for example, to constitute a particular hardware component at one instance of time and to constitute a different hardware component at a different instance of time. Hardware components can provide information to, and receive information from other hardware components. Accordingly, the described hardware components may be regarded as being communicatively coupled. Where multiple hardware components exist contemporaneously, communications may be achieved through signal transmission (e.g., over appropriate circuits and buses 1102) between or among two or more of the hardware components. In embodiments in which multiple hardware components are configured or instantiated at different times, communications between such hardware components may be achieved, for example, through the storage and retrieval of information in memory structures to which the multiple hardware components have access. For example, one hardware component may perform an operation and store the output of that operation in a memory device to which it is communicatively coupled. A further hardware component may then, at a later time, access the memory device to retrieve and process the stored output. Hardware components may also initiate communications with input or output devices, and can operate on a resource (e.g., a collection of information). The various operations of example methods described herein may be performed, at least partially, by one or more processors 1104 that are temporarily configured (e.g., by software) or permanently configured to perform the relevant operations. Whether temporarily or permanently configured, such processors 1104 may constitute processor-implemented components that operate to perform one or more operations or functions described herein. As used herein, "processor-implemented component" refers to a hardware component implemented using one or more processors 1104. Similarly, the methods described herein may be at least partially processor-implemented, with a particular processor or processors 1104 being an example of hardware. For example, at least some of the operations of a method may be performed by one or more processors 1104 or processor-implemented components. Moreover, the one or more processors 1104 may also operate to support performance of the relevant operations in a "cloud computing" environment or as a "software as a service" (SaaS). For example, at least some of the operations may be performed by a group of computers (as examples of machines 1100 including processors 1104), with these operations being accessible via a network 1132 (e.g., the Internet) and via one or more appropriate interfaces (e.g., an API). The performance of certain of the operations may be distributed among the processors 1104, not only residing within a single machine 1100, but deployed across a number of machines 1100. In some example embodiments, the processors 1104 or processor-implemented components may be located in a single geographic location (e.g., within a home environment, an office environment, or a server farm). In other example embodiments, the processors 1104 or processor-implemented components may be distributed across a number of geographic locations.

"PROCESSOR" in this context refers to any circuit or virtual circuit (a physical circuit emulated by logic executing on an actual processor 1104) that manipulates data values according to control signals (e.g., "commands," "op codes," "machine code," etc.) and which produces corresponding output signals that are applied to operate a machine 1100. A processor 1104 may be, for example, a central processing unit (CPU), a reduced instruction set computing (RISC) processor, a complex instruction set computing (CISC) processor, a graphics processing unit (GPU), a digital signal processor (DSP), an ASIC, a radio-frequency integrated circuit (RFIC) or any combination thereof. A processor 1104 may further be a multi-core processor having two or more independent processors 1104 (sometimes referred to as "cores") that may execute instructions 1110 contemporaneously.

What is claimed is:

1. A behavioral testing system comprising:
    a housing chamber for housing testing animals during periods in which the testing animals are not being observed as part of a scientific study;
    a behavioral testing chamber for administering tests and observing the testing animals as part of the scientific study;
    a filtering chamber coupled to the housing chamber and the behavioral testing chamber to provide a passageway between the behavioral testing chamber and the housing chamber, the filtering chamber including a first gate component that can be configured in an open configuration or a closed configuration to manage access of the testing animals between the housing chamber and the behavioral testing chamber;
    one or more computer processors; and
    one or more computer-readable mediums storing instructions that, when executed by the one or more computer processors, cause the behavioral testing system to perform operations for managing access of the testing animals between the housing chamber and the behavioral testing chamber to automate the scientific study, the operations comprising:
    determining that a first testing animal is in the filtering chamber, wherein a configuration of the first gate component positioned between the filtering chamber and the behavioral testing chamber is in a closed configuration to restrict access to the behavioral testing chamber;
    determining, based on data gathered while the first testing animal is in the filtering chamber, that a set of testing conditions have been satisfied; and
    modifying the configuration of the first gate component from the closed configuration to an open configuration to allow the first testing animal to enter the behavioral testing chamber.

2. The behavioral testing system of claim 1, the operations further comprising:
    in response to determining that the first testing animal is in the filtering chamber, modifying a configuration of a second gate component positioned between the housing chamber and the filtering chamber from the open configuration to a closed configuration to restrict access to the housing chamber.

3. The behavioral testing system of claim 2, wherein determining that the set of testing conditions have been satisfied comprises:
    while both the first gate component and the second gate component are configured in the closed configuration, determining that a number of testing animals in the filtering chamber does not exceed a threshold number of testing animals.

4. The behavioral testing system of claim 1, wherein determining that the set of testing conditions have been satisfied comprises:
    determining a unique identifier associated with the first testing animal;
    accessing a testing log corresponding to the unique identifier associated with the first testing animal, the testing log identifying times at which the first testing animal was tested; and
    determining, based on the testing log, that a threshold period of time has elapsed after the first testing animal was last tested.

5. The behavioral testing system of claim 4, wherein determining the unique identifier associated with the first testing animal comprises:
    receiving, via a receiver, a data transmission transmitted from a transmitting device affixed to the first testing animal, wherein the data transmission includes the unique identifier.

6. The behavioral testing system of claim 1, wherein determining that the set of testing conditions have been satisfied comprises:
    while the first testing animal is in the filtering chamber, determining a batter/charge level of an electronic device attached to the first testing animal; and
    determining that the battery charge level of the electronic device exceeds a threshold battery charge level.

7. The behavioral testing system of claim 1, wherein determining that the set of testing conditions have been satisfied comprises:
    while the first testing animal is in the filtering chamber, measuring a weight of the first testing animal, the weight of the first testing animal being measured using a weight sensor included in the filtering chamber; and
    determining that the weight of the first testing animal exceeds a threshold weight.

8. The behavioral testing system of claim 1, the operations further comprising:
    in response to determining that the set of testing conditions have been satisfied, configuring the behavioral testing chamber into a testing state.

9. The behavioral testing system of claim 1, the operations further comprising:
- after modifying the configuration of the first gate component from the closed configuration to the open configuration, determining that the first testing animal has entered the behavioral testing chamber; and
- in response to determining that the first testing animal has entered the behavioral testing chamber, modifying the configuration of the first gate component from the open configuration to the closed configuration.

10. The behavioral testing system of claim 1, the operations further comprising:
- determining that a second testing animal is in the filtering chamber, wherein the configuration of the first gate component positioned between the filtering chamber and the behavioral testing chamber is in the closed configuration to restrict access to the behavioral testing chamber; and
- determining, based on data gathered while the second testing animal is in the filtering chamber, that the set of testing conditions have not been satisfied, wherein the configuration of the first gate component positioned between the filtering chamber and the behavioral testing chamber is not modified to an open configuration based on determining that the set of testing conditions have not been satisfied.

11. The behavioral testing system of claim 1, wherein the housing chamber includes a power charging source that wirelessly charges battery powered electronic devices attached to the testing while the testing animals are in the housing chamber.

12. The behavioral testing system of claim 11, wherein the power charging source is an inductive coil.

13. The behavioral testing system of claim 1, wherein the behavioral testing chamber includes one or more sensors for observing the testing animals as part of a scientific study while the testing animals are in the behavioral testing chamber.

14. The behavioral testing system of claim 13, wherein the one or more sensors includes at least one of a video sensor, a microphone, a heat sensor, and a motion sensor.

15. The behavioral testing system of claim 1, wherein the behavioral testing chamber includes a testing response management component that is a physical mechanism for providing a testing response to testing animals as part of a scientific study.

16. The behavioral testing system of claim 15, wherein the testing response is food or liquid provided to the testing animals as a reward.

17. The behavioral testing system of claim 15, wherein the testing response is an adverse stimuli.

18. The behavioral testing system of claim 17, wherein the adverse stimuli is one of an electric shock, light, or sound.

19. The behavioral testing system of claim 15, wherein testing response management component provides the testing response to a testing animal by transmitting a wireless communication to an electronic device attached to the testing animal to cause the electronic device to provide a perturbation to a specified area of a brain of the testing animal.

20. The behavioral testing system of claim 19, wherein the perturbation comprises at least one of an electrical stimulation, drug delivery, optogenetics, chemogenetics, or neural perturbation.

* * * * *